United States Patent
Baker et al.

(10) Patent No.: US 10,414,784 B2
(45) Date of Patent: *Sep. 17, 2019

(54) AMINOBISPHOSPHONATE ANTIWEAR ADDITIVES

(71) Applicant: Afton Chemical Corporation, Richmond, VA (US)

(72) Inventors: John Marshall Baker, Bracknell (GB); Guillaume Carpentier, Berkshire (GB)

(73) Assignee: Afton Chemical Corporation, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/105,675

(22) Filed: Aug. 20, 2018

(65) Prior Publication Data

US 2018/0370998 A1  Dec. 27, 2018

Related U.S. Application Data

(63) Continuation of application No. 15/706,498, filed on Sep. 15, 2017, now Pat. No. 10,072,032.

(60) Provisional application No. 62/396,465, filed on Sep. 19, 2016.

(51) Int. Cl.
*C07F 9/40* (2006.01)
*C10M 137/12* (2006.01)

(52) U.S. Cl.
CPC .......... *C07F 9/4075* (2013.01); *C07F 9/4006* (2013.01); *C10M 137/12* (2013.01); *C10M 2203/10* (2013.01); *C10M 2203/102* (2013.01); *C10M 2203/1006* (2013.01); *C10M 2207/026* (2013.01); *C10M 2207/028* (2013.01); *C10M 2207/125* (2013.01); *C10M 2209/084* (2013.01); *C10M 2209/104* (2013.01); *C10M 2209/107* (2013.01); *C10M 2215/064* (2013.01); *C10M 2215/28* (2013.01); *C10M 2219/022* (2013.01); *C10M 2223/049* (2013.01); *C10M 2223/06* (2013.01); *C10N 2220/022* (2013.01); *C10N 2230/06* (2013.01); *C10N 2240/04* (2013.01); *C10N 2240/042* (2013.01); *C10N 2240/044* (2013.01); *C10N 2240/045* (2013.01); *C10N 2240/08* (2013.01); *C10N 2240/102* (2013.01); *C10N 2240/104* (2013.01); *C10N 2240/30* (2013.01); *C10N 2270/02* (2013.01)

(58) Field of Classification Search
CPC .......................... C10M 2223/04; C07F 9/4006
USPC .................................. 508/422, 425; 558/135
See application file for complete search history.

(56) References Cited

U.S. PATENT DOCUMENTS

| | | | | |
|---|---|---|---|---|
| 2,870,190 A | * | 1/1959 | Burgert | C07F 9/4006 558/135 |
| 3,170,913 A | * | 2/1965 | De Benneville | C07F 9/3808 521/108 |
| 3,549,728 A | * | 12/1970 | Balde | C07F 9/4009 252/78.5 |
| 4,013,813 A | * | 3/1977 | LeBlanc | D06M 13/447 252/608 |
| 2002/0042539 A1 | * | 4/2002 | Arstad | C07B 59/004 562/21 |

(Continued)

*Primary Examiner* — Vishal V Vasisth
(74) *Attorney, Agent, or Firm* — Brinks Gilson & Lione

(57) ABSTRACT

The present invention relates to novel aminobisphosphonate compounds useful as antiwear and/or friction modifier additive components, lubricant additive compositions and lubricant compositions each comprising such compounds, and methods for making and using the same.

29 Claims, 3 Drawing Sheets

(56) References Cited

U.S. PATENT DOCUMENTS

| 2008/0220037 | A1 | | 9/2008 | Denizot |
| 2013/0072407 | A1 | * | 3/2013 | Ryan .................. C07F 9/65846 508/422 |
| 2015/0030541 | A1 | | 1/2015 | Kinoshita |
| 2016/0066579 | A1 | | 3/2016 | Porosa |

* cited by examiner

AMINOBISPHOSPHONATE ANTIWEAR ADDITIVES

CROSS REFERENCE TO RELATED APPLICATIONS

This application is a CON of Ser. No. 15/706,498, filed Sep. 15, 2017, now U.S. Pat. No. 10,072,032, which claims benefit of 62/396,465, filed Sep. 19, 2016.

FIELD

The present invention relates to novel aminobisphosphonate compounds useful as antiwear and/or friction modifier additive components, lubricant additive compositions and lubricant compositions each comprising such compounds, and methods for making and using the same.

BACKGROUND OF THE INVENTION

Industrial and automotive gears are often subjected to pressures and loads that cause wear on the gear surface and/or roller bearing elements. In some cases, the stress imposed on a gear contributes to micropitting, a form of gear fatigue and a common gear failure mode.

Typically, gear systems require a specially formulated fluid to meet performance requirements. To reduce, or even prevent wear, antiwear additives are commonly added to lubricating compositions used to lubricate the gears. When under pressure, these additives form a protective layer on a gear surface. This protective layer separates the gear contact surfaces from one another and thus, reduces wear on those surfaces. However, not all antiwear additives provide effective surface protection.

The present invention provides novel antiwear additives and/or friction modifiers that can be used in lubricant compositions for industrial gears, windturbines, hydraulic devices, and automotive gears to provide reduced wear and/or friction on the gear surface and reduced micropitting of the gears.

SUMMARY OF THE INVENTION

In one aspect, the invention relates to a compound of formula (I):

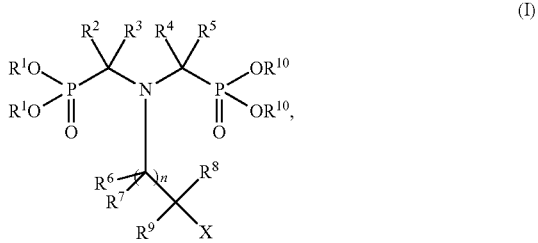

wherein each $R^1$ and $R^{10}$ is the same or different and is independently selected from $C_1$-$C_{20}$ linear alkyl, $C_2$-$C_{20}$ linear alkenyl, $C_3$-$C_{20}$ branched alkyl, and $C_3$-$C_{20}$ branched alkenyl;
n is an integer from 1 to 7;
each of $R^2$, $R^3$, $R^4$, $R^5$, $R^6$, $R^7$, $R^8$, and $R^9$ is the same or different and is each independently selected from H, $C_1$-$C_{10}$ linear alkyl, $C_2$-$C_{10}$ linear alkenyl, $C_3$-$C_{10}$ branched alkyl, and $C_3$-$C_{10}$ branched alkenyl;

X is selected from the group consisting of H, hydroxy, and $N(R^{11})(R^{12})$; and
$R^{11}$ and $R^{12}$ are the same or different and are each independently selected from the group consisting of H, hydroxy, alkyl, alkenyl, and alkynyl.

In a second aspect, the invention provides a lubricant additive concentrate comprising at least one compound of formula (I).

In a third aspect, the invention provides a lubricant additive concentrate comprising at least one compound of formula (I) and one or more additional additives.

In a fourth aspect, the invention provides a lubricant composition comprising a majority amount of base oil and at least one compound of formula (I).

In a fifth aspect, the invention provides a method of lubricating moving metal surfaces of a machine part with a lubricant composition comprising at least one compound of formula (I).

In a sixth aspect, the present invention provides a method of reducing wear on a moving metal surface of a machine part comprising lubricating the machine part with a lubricant composition comprising at least one compound of formula (I).

In another aspect, the present invention provides a method of reducing friction on a moving metal surface of a machine part comprising lubricating the machine part with a lubricant composition comprising at least one compound of formula (I).

In another embodiment the present invention provides a method of lubricating a machine part with a lubricant composition comprising at least one compound of formula (I), wherein the machine part comprises an industrial gear, a windturbine gear, an axle, a differential, an engine, a crankshaft, a transmission, a clutch, a hydraulic apparatus, a slideway apparatus, and/or a turbine.

DETAILED DESCRIPTION OF THE INVENTION

Figure 1:
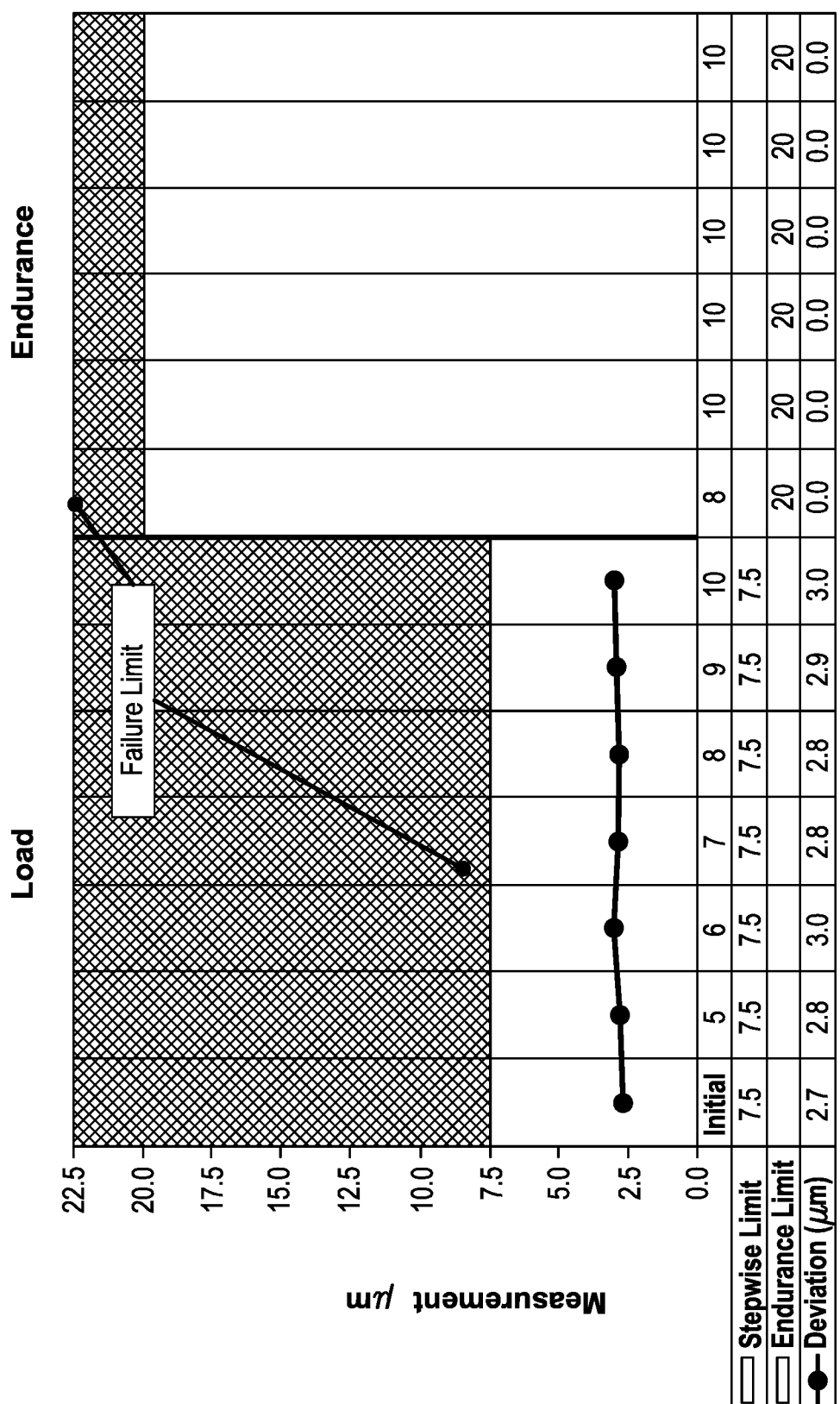
FIG. 1 represents an average profile deviation (ffm) caused by micropitting in a micropitting test for an embodiment of the invention.

The invention disclosed herein relates to novel aminobisphosphonate compounds useful as antiwear and/or friction modifier additive components, lubricant additive concentrates and lubricant compositions, each comprising such compounds, and methods for making and using the same.

Although certain embodiments of the present invention may be described individually herein, it is understood by the skilled artisan that any one embodiment can be combined with any other embodiment or embodiments, and such combinations are within the scope of the instant invention.

Embodiments that relate to a compound of formula (I) include, but are not limited to, the following:

(1) A compound of formula (I):

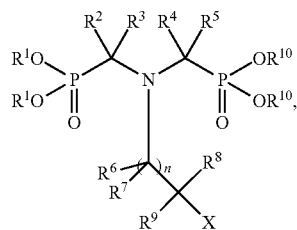

wherein each of $R^1$ and $R^{10}$ is the same or different and is independently selected from $C_1$-$C_{20}$ linear alkyl, $C_2$-$C_{20}$ linear alkenyl, $C_3$-$C_{20}$ branched alkyl, and $C_3$-$C_{20}$ branched alkenyl;
n is an integer from 1 to 7;
each of $R^2$, $R^3$, $R^4$, $R^5$, $R^6$, $R^7$, $R^8$, and $R^9$ is the same or different and is each independently selected from H, $C_1$-$C_{10}$ linear alkyl, $C_2$-$C_{10}$ linear alkenyl, $C_3$-$C_{10}$ branched alkyl, and $C_3$-$C_{10}$ branched alkenyl;
X is selected from the group consisting of H, hydroxy, and $N(R^{11})(R^{12})$; and
$R^{11}$ and $R^{12}$ are the same or different and are each independently selected from the group consisting of H, hydroxy, alkyl, alkenyl, and alkynyl.
(2) The compound of (1), wherein each of $R^1$ and $R^{10}$ is the same or different and is independently selected from $C_2$-$C_{20}$ linear alkyl.
(3) The compound of (1), wherein each of $R^1$ and $R^{10}$ is n-butyl.
(4) The compound of (1), wherein each of $R^1$ and $R^{10}$ is ethyl.
(5) The compound of (1) or (2), wherein each $R^1$ is 2-ethyl hexyl.
(6) The compound of (1) or (2), wherein each $R^{10}$ is 2-ethyl hexyl.
(7) The compound of (1), wherein each of $R^1$ and $R^{10}$ is 2-ethyl hexyl.
(8) The compound of (1), wherein each of $R^1$ and $R^{10}$ is oleyl.
(9) The compound of any one of (1) to (8), wherein each of $R^2$, $R^3$, $R^4$, and $R^5$ are H.
(10) The compound of any one of (1) to (9), wherein each of $R^6$, $R^7$, $R^8$, and $R^9$ are H.
(11) The compound of any one of (1) to (10), wherein n is an integer from 1 to 4.
(12) The compound of (11), wherein n is 1 or 2.
(13) The compound of (1), wherein (a) each of $R^1$ and $R^{10}$ is the same or different and is independently selected from $C_2$-$C_{20}$ linear alkyl; and (b) each of $R^2$, $R^3$, $R^4$, $R^5$, $R^6$, $R^7$, $R^8$, and $R^9$ are H.
(14) The compound of (13), wherein each of $R^1$ and $R^{10}$ is the same or different and is independently selected from $C_2$-$C_{10}$ linear alkyl.
(15) The compound of (13) or (14), wherein (c) n is an integer from 1 to 4.
(16) The compound of (15), wherein n is 1 or 2.
(17) The compound of any one of (1) to (16), wherein X is hydroxyl.
(18) The compound of any one of (1) to (16), wherein X is $N(R^{11})(R^{12})$.
(19) The compound of (18), wherein $R^{11}$ and $R^{12}$ are the same or different and are $C_1$-$C_4$ alkyl.
(20) The compound of (19), wherein $R^{11}$ and $R^{12}$ are both methyl.
(21) The compound of any one of (1) to (16), wherein X is H.
(22) The compound of (1), wherein the compound of formula (I) is selected from:

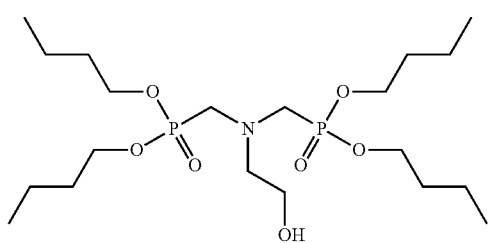

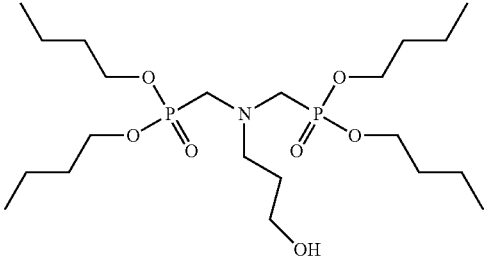

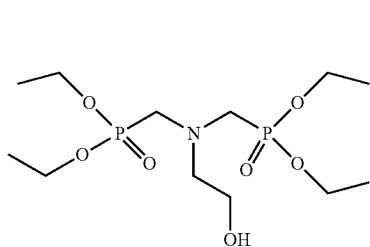

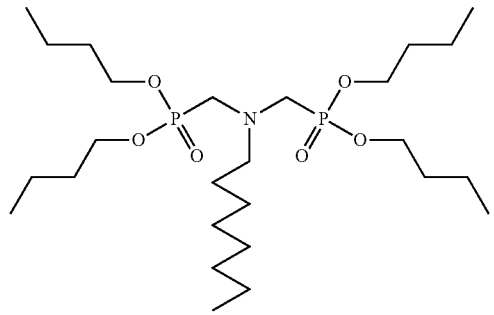

(23) The compound of (1), wherein the compound of formula (I) is selected from

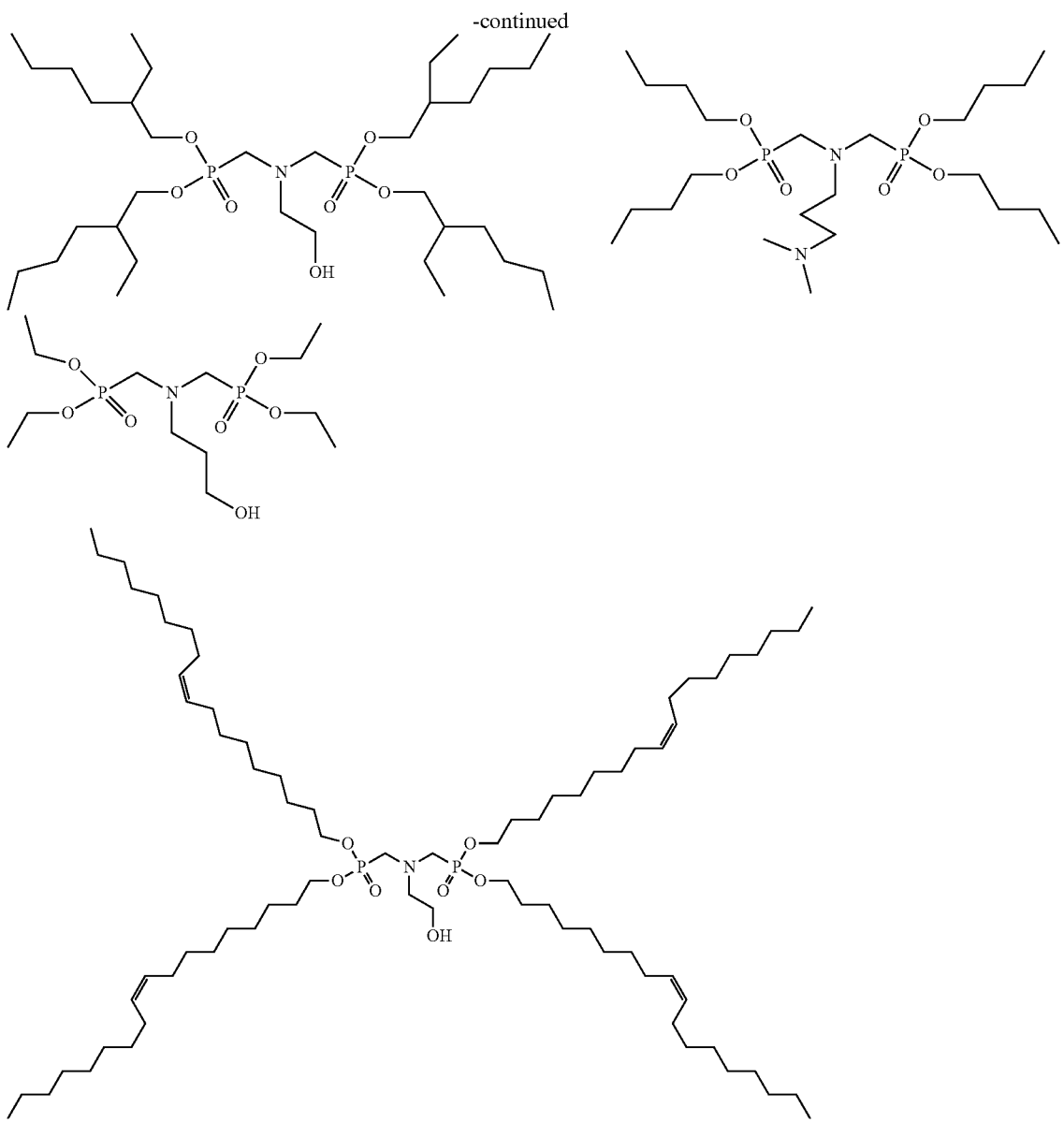

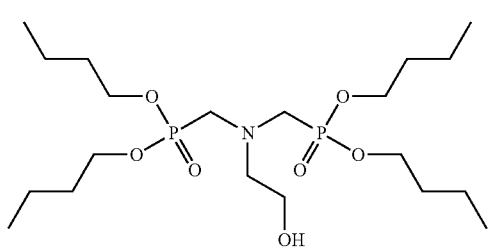

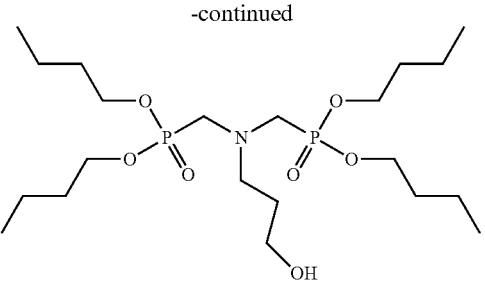

In one embodiment, the present invention relates to a lubricant additive concentrate comprising a compound of formula (I).

In one embodiment, the compound of formula (I) is present in the lubricant additive concentrate in an amount from about 0.01 wt % to about 3 wt % based on the total weight of the lubricant composition.

In another embodiment, the lubricant additive concentrate further comprises one or more additive components selected from the group consisting of an antioxidant, an additional antiwear agent, a corrosion inhibitor, a detergent, an extreme pressure agent, a dispersant, a viscosity index improver, and a friction modifier.

In one embodiment, a lubricant composition of the present invention comprises a major amount of base oil of lubricating viscosity or a grease prepared therefrom and the compound of formula (I).

In one embodiment, a compound of formula (I) is present in a lubricant composition in such an amount as to provide between 100-1200 ppm of phosphorus to the lubricant.

In another embodiment, the lubricant composition further comprises one or more additive components selected from the group consisting of an antioxidant, an additional antiwear agent, a corrosion inhibitor, a detergent, an extreme pressure agent, dispersant, a viscosity index improver, and a friction modifier.

In another embodiment, the method of the present invention for reducing wear on a metal surface of a machine part includes lubricating the machine part with a lubricant having an effective amount of a compound of formula (I) wherein the compound of formula (I) is selected from the group consisting of:

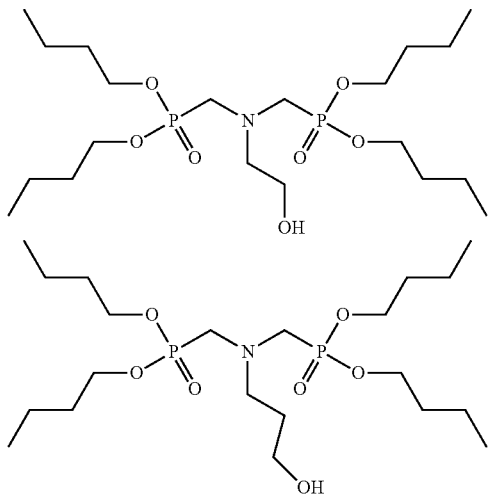

In one embodiment, the machine part is selected from one or more of an industrial gear, a windturbine gear, an axle, a differential, an engine, a crankshaft, a transmission, a clutch, a hydraulic apparatus, a slideway apparatus, and a turbine.

A method of reducing wear between moving metal surfaces of a machine part comprises lubricating the machine part with a lubricant composition comprising a major amount of a base oil of lubricating viscosity or a grease prepared therefrom and an effective amount of a compound of formula (I).

In one preferred aspect the present invention provides the use of a compound of formula (I) to reduce wear between moving metal surfaces, and/or to reduce friction between moving metal surfaces. For instance, the present invention provides the use of a compound of formula (I) to reduce micropitting. This preferred aspect of the invention may underlie any of the methods of the invention disclosed herein.

In certain embodiments, the lubricant additive concentrates or the lubricant compositions comprise at least one compound of formula (I) and further comprise one or more additive components. Such concentrates or compositions can comprise one or more components with the same or different properties. For example, concentrates and lubricant compositions comprising one or more compounds of formula (I) and one or more additive components, such as one, two or more antioxidants, dispersants, detergents etc. are within the scope of the present invention.

As used herein, the term "alkyl," as well as the alkyl moieties of other groups referred herein, are linear or branched saturated hydrocarbons. Alkyl may preferably contain from 1 to 30 carbon atoms, such as 1 to 20 carbon atoms, or 1 to 10 carbon atoms, unless otherwise specified. Representative examples of alkyl groups include, but are not limited to, methyl, ethyl, propyl, butyl, pentyl, neopentyl, 2-ethylhexyl, and the like.

As used herein, the term "alkenyl" means a straight or branched hydrocarbon chain containing at least one carbon-carbon double bond. Unless indicated otherwise, alkenyl may preferably contain from 2 to 30 carbon atoms, such as 2 to 20 carbon atoms, or 2 to 10 carbon atoms. For example, the term "$C_2$-$C_4$ alkenyl" means an alkenyl group containing 2-4 carbon atoms. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, oleyl, 3-decenyl, olelyl, and the like.

As used herein, the term "alkynyl" means a straight or branched hydrocarbon chain containing at least one carbon-carbon triple bond. Unless indicated otherwise, alkynyl may preferably contain from 2 to 30 or 3 to 30 carbon atoms, such as 2 to 20 or 3 to 20 carbon atoms, or from 2 to 10 or 3 to 10 carbon atoms. For example, the term "$C_2$-$C_4$ alkynyl" means an alkynyl group containing 2-4 carbon atoms. Representative examples of alkynyl include, but are not limited to, ethynyl, 2-propynyl, 3-butynyl, 4-pentynyl, 5-hexynyl, 2-heptynyl, 3-decynyl, and the like.

As used herein, the term "about" means, with respect to an amount, approximate or almost, and includes an exact amount. For example, the phrase "about 1.0%" means approximately or almost 1.0% but also includes exactly 1.0%.

As used herein, the phrase "effective amount" means an amount of a compound that achieves the desired effect, such as reducing wear and/or friction.

The compounds of formula (I) are contemplated for use as an additive in lubricating base oil. As used herein, the term "base oil" or "base stock" refers to oils categorized by the American Petroleum Institute (API) category groups Group I-V oils as well as animal oils, vegetable oils (e.g. castor oil and lard oil), petroleum oils, mineral oils, synthetic oils, and oils derived from coal or shale. The American Petroleum Institute has categorized these different base stock types as follows: Group I, greater than 0.03 wt percent sulfur, and/or less than 90 vol percent saturates, viscosity index greater than or equal to 80 and less than 120; Group II, less than or equal to 0.03 wt percent sulfur, and greater than or equal to 90 vol percent saturates, viscosity index greater than or equal to 80 and 120; Group III, less than or equal to 0.03 wt percent sulfur, and greater than or equal to 90 vol percent saturates, viscosity index greater than or equal to 120; Group IV, all polyalphaolefins; Group V base stock encompasses all other base stocks which cannot be classified as Group I, II, III, or IV base stocks. Group V base stocks include but are not limited to naphthenic oils and esters. Hydrotreated base stocks and catalytically dewaxed base stocks, because of their low sulfur and aromatics content, generally fall into the Group II and Group III categories. Polyalphaolefins (Group IV basestocks) are synthetic base oils prepared from various alpha olefins and are substantially free of sulfur and aromatics.

Groups I, II, and III are mineral oil process stocks. Group IV base oils contain true synthetic molecular species, which are produced by polymerization of olefinically unsaturated hydrocarbons. Many Group V base oils are also true synthetic products and may include diesters, polyol esters, polyalkylene glycols, alkylated aromatics, polyphosphate esters, polyvinyl ethers, and/or polyphenyl ethers, and the like, but may also be naturally occurring oils, such as vegetable oils. It should be noted that although Group III base oils are derived from mineral oil, the rigorous processing that these fluids undergo causes their physical properties to be very similar to some true synthetics, such as PAOs. Therefore, oils derived from Group III base oils may sometimes be referred to as synthetic fluids in the industry.

The compounds of formula (I) can be added to base oils in the form of a mineral oil or synthetic oil, animal oil, vegetable oil, or mixtures thereof. In general, the mineral oils, both paraffinic and naphthenic and mixtures thereof can be employed as lubricating oil or as the grease vehicle. Also contemplated are greases in which any of the foregoing oils are employed as a base.

The compound of formula (I), in addition to other additive components, can be added to a lubricating oil to form a finished fluid. In certain embodiments, the finished fluid has a viscosity of ISO 10 VG through ISO 680 VG. In one embodiment, the finished fluid comprises a lubricating oil and a compound of formula (I) and has a viscosity of ISO 68 VG through ISO 680 VG. In another embodiment, the finished fluid comprises a lubricating oil and a compound of formula (I) and has a viscosity of ISO 22 VG through ISO 68 VG. In another embodiment, the lubricating composition comprises a lubricating oil and a compound of formula (I) and has an SAE gear viscosity number of at least about SAE 70W, or at least about SAE 75W. The lubricating composition may also have a multigrade rating such as SAE 75W-80, 75W-90, 75W-140, 80W-90, 80W-40, 85W-90, 80W-90, or 80W-140. Multigrade lubricants may include a viscosity improver which is formulated with the oil of lubricating viscosity to provide the above lubricant grades.

Where the lubricant is employed as a grease, the lubricant is generally used in an amount sufficient to balance the total grease composition, after accounting for the desired quantity of the thickening agent, and other additive components included in the grease formulation. A wide variety of materials can be employed as thickening or gelling agents. These can include any of the conventional metal salts or soaps, such as calcium, or lithium stearates or hydroxystearates, which are dispersed in the lubricating vehicle in grease-forming quantities in an amount sufficient to impart to the resulting grease composition the desired consistency. Other thickening agents that can be employed in the grease formulation comprise the non-soap thickeners, such as surface-modified clays and silicas, aryl ureas, calcium complexes and similar materials. In general, grease thickeners can be employed which do not melt or dissolve when used at the required temperature within a particular environment; however, in all other respects, any material which is normally employed for thickening or gelling hydrocarbon fluids for forming greases can be used in a grease comprising the compound of formula (I).

Where synthetic oils, or synthetic oils employed as the vehicle for the grease, are desired in preference to mineral oils, or in mixtures of mineral and synthetic oils, various synthetic oils may be used. Typical synthetic oils include polyisobutylenes, polybutenes, polydecenes, siloxanes and silicones (polysiloxanes).

The present invention provides lubricant compositions comprising a major amount of oil of lubricating viscosity or a grease prepared therefrom and a minor amount of a compound of formula (I). The compound of formula (I) can be added to a major amount of oil of lubricating viscosity, or grease prepared therefrom, as a single compound or as a component of a lubricant additive concentrate. As used herein, a major amount of oil or grease means that the oil or grease in the composition is in the composition in an amount that is greater than the amount of compound of formula (I). Typically, the amount of the oil/grease is at least 50% by weight of the overall composition, such as at least 70% or at least 90%. Similarly, if the compound of formula (I) is a component of a lubricant additive concentrate and the lubricant additive concentrate is added to the oil or grease, a major amount of oil or grease means the amount of oil or grease in the lubricant composition is more than the amount of lubricant additive concentrate in the lubricant composition. The compound of formula (I) can be in the lubricant composition in an amount between about 0.001% to 10%, between 0.005% to 5%, between 0.01% to 2.0%, between 0.5% to 2.0%, and between 0.015% to about 0.6% by weight of the total composition. In some embodiments, lubricating compositions can contain between about from 0.005% to 0.6%, between about 0.06 and about 0.6 wt %, or between about 0.02 and about 0.5 wt %, or between about 0.005 and about 0.2 wt % of the compound of formula (I).

As mentioned above, the compounds of formula (I) can be readily formulated into lubricant compositions suitable for use with a variety of machine parts and components. The lubricant compositions comprising a compound of formula (I) can optionally further comprise one or more other additive components or diluent oil. The list of additive components disclosed below is not exhaustive and additive components not expressly disclosed herein are well known to the skilled artisan and may also be included in the lubricant compositions. Without limitation, additive components that can be used in the lubricant compositions of the present invention include antioxidants, additional antiwear agents, corrosion inhibitors, detergents, dispersants, extreme pressure agents, viscosity index improvers, pour point depressants, antifoam agents, and friction reducers.

In one embodiment the present invention provides a lubricant additive concentrate comprising a compound of formula (I) and at least one additional additive component and/or diluent oil. The one or more additional additive component(s) can be selected from an antioxidant, an additional antiwear agent, a corrosion inhibitor, a detergent, a dispersant, an extreme pressure agent, a viscosity index improver, a pour point depressant, a demulsifier, an antifoam agent, and a friction modifier. The diluent oil can be any suitable oil of lubricating viscosity or grease prepared therefrom.

The compounds of formula (I) can be directly incorporated into an oil of lubricating viscosity. Alternatively, compounds of formula (I) can be prepared in combination with one or more diluent oils and/or other lubricant additives to form a lubricant additive concentrate. Generally, the lubricant additive concentrate will further be incorporated into the oil of lubricating viscosity at a particular weight percent (wt %) of the lubricant additive concentrate relative to the total weight of the final lubricant composition. The wt % selected is generally referred to as the treat rate and the lubricant composition containing the lubricant additive concentrate is generally referred to as a finished fluid.

Antioxidants

Antioxidant compounds are known and include, for example, phenates, phenate sulfides, sulfurized olefins, phosphosulfurized terpenes, sulfurized esters, aromatic amines, alkylated diphenylamines (e.g., nonyl diphenylamine, di-nonyl diphenylamine, octyl diphenylamine, di-octyl diphenylamine), phenyl-alpha-naphthylamines, alkylated phenyl-alpha-naphthylamines, hindered non-aromatic amines, phenols, hindered phenols, oil-soluble molybdenum compounds, macromolecular antioxidants, or mixtures thereof. A single antioxidant or a combination of two or more can be used.

The hindered phenol antioxidant may contain a secondary butyl and/or a tertiary butyl group as a sterically hindering group. The phenol group may be further substituted with a hydrocarbyl group and/or a bridging group linking to a second aromatic group. Examples of suitable hindered phenol antioxidants include 2,6-di-tert-butylphenol, 4-methyl-2,6-di-tert-butylphenol, 4-ethyl-2,6-di-tert-butylphenol, 4-propyl-2,6-di-tert-butylphenol or 4-butyl-2,6-di-tert-butylphenol, or 4-dodecyl-2,6-di-tert-butylphenol. In an embodiment the hindered phenol antioxidant may be an ester and may include, e.g., an addition product derived from 2,6-di-tert-butylphenol and an alkyl acrylate, wherein the alkyl group may contain about 1 to about 18, or about 2 to about 12, or about 2 to about 8, or about 2 to about 6, or about 4 carbon atoms.

Useful antioxidants may include diarylamines and high molecular weight phenols. In an embodiment, the lubricating oil composition may contain a mixture of a diarylamine and a high molecular weight phenol, such that each antioxidant may be present in an amount sufficient to provide up to about 5%, by weight of the antioxidant, based upon the final weight of the lubricating oil composition. In some embodiments, the antioxidant may be a mixture of about 0.3 to about 1.5% diarylamine and about 0.4 to about 2.5% high molecular weight phenol, by weight, based upon the final weight of the lubricating oil composition.

Examples of suitable olefins that may be sulfurized to form a sulfurized olefin include propylene, butylene, isobutylene, polyisobutylene, pentene, hexene, heptene, octene, nonene, decene, undecene, dodecene, tridecene, tetradecene, pentadecene, hexadecene, heptadecene, octadecene, nonadecene, eicosene or mixtures thereof. In an embodiment, hexadecene, heptadecene, octadecene, nonadecene, eicosene or mixtures thereof and their dimers, trimers and tetramers are especially useful olefins. Alternatively, the olefin may be a Diels-Alder adduct of a diene such as 1,3-butadiene and an unsaturated ester, such as, butylacrylate.

Another class of sulfurized olefin includes sulfurized fatty acids and their esters. The fatty acids are often obtained from vegetable oil or animal oil and typically contain about 4 to about 22 carbon atoms. Examples of suitable fatty acids and their esters include triglycerides, oleic acid, linoleic acid, palmitoleic acid or mixtures thereof. Often, the fatty acids are obtained from lard oil, tall oil, peanut oil, soybean oil, cottonseed oil, sunflower seed oil or mixtures thereof. Fatty acids and/or ester may be mixed with olefins, such as α-olefins.

The one or more antioxidant(s) may be present in ranges of from about 0 wt. % to about 20 wt. %, or about 0.1 wt. % to about 10 wt. %, or about 0.5 wt. % to about 5 wt. %, in the lubricating composition.

Additional Antiwear Agents

Examples of additional suitable antiwear agents include, but are not limited to, a metal thiophosphate; a metal dialkyldithiophosphate; a phosphoric acid ester or salt thereof; a phosphate ester(s); a phosphite; a phosphorus-containing carboxylic ester, ether, or amide; a sulfurized olefin; thiocarbamate-containing compounds including, thiocarbamate esters, alkylene-coupled thiocarbamates, and bis(S-alkyldithiocarbamyl)disulfides; and mixtures thereof. The phosphorus containing antiwear agents are more fully described in European Patent No. 0612 839. The metal in the dialkyl dithio phosphate salts may be an alkali metal, alkaline earth metal, aluminum, lead, tin, molybdenum, manganese, nickel, copper, titanium, or zinc. A useful antiwear agent may be a zinc dialkyldithiophosphate.

The additional antiwear agent may be present in ranges of from about 0 wt. % to about 15 wt. %, or about 0.05 wt. % to about 10 wt. %, or about 0.01 wt. % to about 5 wt. %, or about 0.1 wt. % to about 3 wt. % of the total weight of the lubricating composition.

Detergents

The lubricant composition may optionally comprise one or more neutral, low based, or overbased detergents, and mixtures thereof. Suitable detergent substrates include phenates, sulfur containing phenates, sulfonates, calixarates, salixarates, salicylates, carboxylic acids, phosphorus acids, mono- and/or di-thiophosphoric acids, alkyl phenols, sulfur coupled alkyl phenol compounds and methylene bridged phenols. Suitable detergents and their methods of preparation are described in greater detail in numerous patent publications, including U.S. Pat. No. 7,732,390, and references cited therein.

The detergent substrate may be salted with an alkali or alkaline earth metal such as, but not limited to, calcium, magnesium, potassium, sodium, lithium, barium, or mixtures thereof. In some embodiments, the detergent is free of barium. A suitable detergent may include alkali or alkaline earth metal salts of petroleum sulfonic acids and long chain mono- or di-alkylarylsulfonic acids with the aryl group being one of benzyl, tolyl, and xylyl.

Overbased detergent additives are well known in the art and may be alkali or alkaline earth metal overbased detergent additives. Such detergent additives may be prepared by reacting a metal oxide or metal hydroxide with a substrate and carbon dioxide gas. The substrate is typically an acid, for example, an acid such as an aliphatic substituted sulfonic acid, an aliphatic substituted carboxylic acid, or an aliphatic substituted phenol.

The terminology "overbased" relates to metal salts, such as metal salts of sulfonates, carboxylates, and phenates, wherein the amount of metal present exceeds the stoichiometric amount. Such salts may have a conversion level in excess of 100% (i.e., they may comprise more than 100% of the theoretical amount of metal needed to convert the acid to its "normal," "neutral" salt). The expression "metal ratio," often abbreviated as MR, is used to designate the ratio of total chemical equivalents of metal in the overbased salt to chemical equivalents of the metal in a neutral salt according to known chemical reactivity and stoichiometry. In a normal or neutral salt, the metal ratio is one and in an overbased salt, the MR, is greater than one. Such salts are commonly referred to as overbased, hyperbased, or superbased salts and may be salts of organic sulfur acids, carboxylic acids, or phenols.

The overbased detergent may have a metal ratio of from 1.1:1, or from 2:1, or from 4:1, or from 5:1, or from 7:1, or from 10:1.

In some embodiments, a detergent can be used for reducing or preventing rust in a gear, axle, or engine.

The detergent may be present at about 0 wt. % to about 10 wt. %, or about 0.1 wt. % to about 8 wt. %, or about 1 wt. % to about 4 wt. %, based on the total weight of the lubricant composition.

Dispersants

The lubricant composition may optionally further comprise one or more dispersants or mixtures thereof. Dispersants are often known as ashless-type dispersants because, prior to mixing in a lubricating oil composition, they do not contain ash-forming metals and they do not normally contribute any ash when added to a lubricant. Ashless-type dispersants are characterized by a polar group attached to a relatively high molecular or weight hydrocarbon chain. Typical ashless dispersants include N-substituted long chain alkenyl succinimides. Examples of N-substituted long chain alkenyl succinim ides include polyisobutylene succinimide with number average molecular weight of the polyisobutylene substituent in a range of about 350 to about 5000, or about 500 to about 3000. Succinimide dispersants and their preparation are disclosed, for instance in U.S. Pat. Nos. 7,897,696 and 4,234,435. Succinimide dispersants are typically an imide formed from a polyamine, typically a poly (ethyleneamine).

In some embodiments the lubricant composition comprises at least one polyisobutylene succinimide dispersant derived from polyisobutylene with number average molecular weight in the range about 350 to about 5000, or about 500 to about 3000. The polyisobutylene succinimide may be used alone or in combination with other dispersants.

In some embodiments, polyisobutylene (PIB), when included, may have greater than 50 mol %, greater than 60 mol %, greater than 70 mol %, greater than 80 mol %, or greater than 90 mol % content of terminal double bonds. Such a PIB is also referred to as highly reactive PIB ("HR-PIB"). HR-PIB having a number average molecular weight ranging from about 800 to about 5000 is suitable for use in embodiments of the present disclosure. Conventional non-highly reactive PIB typically has less than 50 mol %, less than 40 mol %, less than 30 mol %, less than 20 mol %, or less than 10 mol % content of terminal double bonds.

An HR-PIB having a number average molecular weight ranging from about 900 to about 3000 may be suitable. Such an HR-PIB is commercially available, or can be synthesized by the polymerization of isobutene in the presence of a non-chlorinated catalyst such as boron trifluoride, as described in U.S. Pat. Nos. 4,152,499 and 5,739,355. When used in the aforementioned thermal ene reaction, HR-PIB may lead to higher conversion rates in the reaction, as well as lower amounts of sediment formation, due to increased reactivity.

One class of suitable dispersants may be Mannich bases. Mannich bases are materials that are formed by the condensation of a higher molecular weight, alkyl substituted phenol, a polyalkylene polyamine, and an aldehyde such as formaldehyde. Mannich bases are described in more detail in U.S. Pat. No. 3,634,515.

A suitable class of dispersants may be high molecular weight esters or half ester amides.

The dispersants may also be post-treated by conventional methods by reaction with any of a variety of agents. Among these agents are boron, urea, thiourea, dimercaptothiadiazoles, carbon disulfide, aldehydes, ketones, carboxylic acids, hydrocarbon-substituted succinic anhydrides, maleic anhydride, nitriles, epoxides, carbonates, cyclic carbonates, hindered phenolic esters, and phosphorus compounds. U.S. Pat. Nos. 7,645,726; 7,214,649; and 8,048,831 describe some suitable post-treatment methods and post-treated products.

The dispersant, if present, can be used in an amount sufficient to provide up to about 20 wt. %, based upon the total weight of the lubricating oil composition. The amount of the dispersant that can be used may be about 0.1 wt. % to about 15 wt. %, or about 0.1 wt. % to about 10 wt. %, or about 3 wt. % to about 10 wt. %, or about 1 wt. % to about 6 wt. %, or about 7 wt. % to about 12 wt. %, based upon the total weight of the lubricating oil composition. In an embodiment, the lubricating oil composition utilizes a mixed dispersant system.

Extreme Pressure Agents

The lubricating oil compositions herein also may optionally contain one or more extreme pressure agents. Extreme Pressure (EP) agents that are soluble in the oil include sulfur- and chlorosulfur-containing EP agents, chlorinated hydrocarbon EP agents and phosphorus EP agents. Examples of such EP agents include chlorinated waxes; organic sulfides and polysulfides such as dibenzyldisulfide, bis(chlorobenzyl) disulfide, dibutyl tetrasulfide, sulfurized methyl ester of oleic acid, sulfurized alkylphenol, sulfurized dipentene, sulfurized terpene, and sulfurized Diels-Alder adducts; phosphosulfurized hydrocarbons such as the reaction product of phosphorus sulfide with turpentine or methyl oleate; phosphorus esters such as the dihydrocarbyl and trihydrocarbyl phosphites, e.g., dibutyl phosphite, diheptyl phosphite, dicyclohexyl phosphite, pentylphenyl phosphite; dipentylphenyl phosphite, tridecyl phosphite, distearyl phosphite and polypropylene substituted phenyl phosphite; metal thiocarbamates such as zinc dioctyldithiocarbamate and barium heptylphenol diacid; amine salts of alkyl and dialkylphosphoric acids, including, for example, the amine salt of the reaction product of a dialkyldithiophosphoric acid with propylene oxide; and mixtures thereof.

The EP agent may be present in ranges of from about 0 wt. % to about 15 wt. %, or about 0.05 wt. % to about 10 wt. %, or about 0.01 wt. % to about 5 wt. %, or about 0.1 wt. % to about 3 wt. % of the total weight of the lubricating composition.

Additional Friction Modifiers

The lubricating oil compositions herein may also optionally contain one or more additional friction modifiers. Suitable friction modifiers may comprise metal containing and metal-free friction modifiers and may include, but are not limited to, imidazolines, amides, amines, succinimides, alkoxylated amines, alkoxylated ether amines, amine oxides, amidoamines, nitriles, betaines, quaternary amines, imines, amine salts, amino guanidines, alkanolamides, phosphonates, metal-containing compounds, glycerol esters, sulfurized fatty compounds and olefins, sunflower oil and other naturally occurring plant or animal oils, dicarboxylic acid esters, esters or partial esters of a polyol and one or more aliphatic or aromatic carboxylic acids, and the like.

Suitable friction modifiers may contain hydrocarbyl groups that are selected from straight chain, branched chain, or aromatic hydrocarbyl groups or mixtures thereof, and may be saturated or unsaturated. The hydrocarbyl groups may be composed of carbon and hydrogen or hetero atoms such as sulfur or oxygen. The hydrocarbyl groups may range from about 12 to about 25 carbon atoms. In an embodiment the friction modifier may be a long chain fatty acid ester. In an embodiment the long chain fatty acid ester may be a mono-ester, or a di-ester, or a (tri)glyceride. The friction modifier may be a long chain fatty amide, a long chain fatty ester, a long chain fatty epoxide derivative, or a long chain imidazoline.

Other suitable friction modifiers may include organic, ashless (metal-free), nitrogen-free organic friction modifiers. Such friction modifiers may include esters formed by reacting carboxylic acids and anhydrides with alkanols and generally include a polar terminal group (e.g. carboxyl or hydroxyl) covalently bonded to an oleophilic hydrocarbon chain. An example of an organic ashless nitrogen-free friction modifier is known generally as glycerol monooleate (GMO) which may contain mono-, di-, and tri-esters of oleic acid. Other suitable friction modifiers are described in U.S. Pat. No. 6,723,685.

Aminic friction modifiers may include amines or polyamines. Such compounds can have hydrocarbyl groups that are linear, either saturated or unsaturated, or a mixture thereof and may contain from about 12 to about 25 carbon atoms. Further examples of suitable friction modifiers include alkoxylated amines and alkoxylated ether amines. Such compounds may have hydrocarbyl groups that are linear, either saturated, unsaturated, or a mixture thereof. They may contain from about 12 to about 25 carbon atoms. Examples include ethoxylated amines and ethoxylated ether amines.

The amines and amides may be used as such or in the form of an adduct or reaction product with a boron compound such as a boric oxide, boron halide, metaborate, boric acid or a mono-, di- or tri-alkyl borate. Other suitable friction modifiers are described in U.S. Pat. No. 6,300,291.

A friction modifier may be present in amounts of about 0 wt. % to about 10 wt. %, or about 0.01 wt. % to about 8 wt. %, or about 0.1 wt. % to about 4 wt. %, based on the total weight of the lubricant composition.

Viscosity Index Improvers

The lubricating oil compositions herein also may optionally contain one or more viscosity index improvers. Suitable viscosity index improvers may include polyolefins, olefin copolymers, ethylene/propylene copolymers, polyisobutenes, hydrogenated styrene-isoprene polymers, styrene/maleic ester copolymers, hydrogenated styrene/butadiene copolymers, hydrogenated isoprene polymers, alpha-olefin maleic anhydride copolymers, polymethacrylates, polyacrylates, polyalkyl styrenes, hydrogenated alkenyl aryl conjugated diene copolymers, or mixtures thereof. Viscosity index improvers may include star polymers and suitable examples are described in US Publication No. 2012/0101017 A1.

The lubricating oil compositions herein also may optionally contain one or more dispersant viscosity index improvers in addition to a viscosity index improver or in lieu of a viscosity index improver. Suitable dispersant viscosity index improvers may include functionalized polyolefins, for example, ethylene-propylene copolymers that have been functionalized with the reaction product of an acylating agent (such as maleic anhydride) and an amine; polymethacrylates functionalized with an amine, or esterified maleic anhydride-styrene copolymers reacted with an amine.

The total amount of viscosity index improver and/or dispersant viscosity index improver may be about 0 wt. % to about 20 wt. %, about 0.1 wt. % to about 15 wt. %, about 0.1 wt. % to about 12 wt. %, or about 0.5 wt. % to about 10 wt. % based on the total weight, of the lubricating composition.

Effective amounts of the various additive components for a specific formulation may be readily ascertained, but for illustrative purposes these general guides for representative effective amounts are provided. The amounts below are given in weight % of the finished fluid.

| Component | Example Ranges (wt %) | Example Ranges (wt %) |
|---|---|---|
| A compound of formula (I) | 0.01-2 | 0.06-0.6 |
| Dispersant | 0-20 | 0.05-0.5 |
| Extreme Pressure Agent | 0-5 | 0.5-2.0 |
| Rust Inhibitor | 0-1.0 | 0.05-1.0 |
| Corrosion Inhibitor | 0-5 | 0.05-1.0 |
| Demulsifier | 0-5 | 0.002-0.05 |
| Antifoam Agent | 0-0.5 | 0.001-0.1 |
| Diluent | 0-10 | 1.0-5.0 |
| Anti-Oxidant | 0-5 | 0.05-0.3 |
| Lubricating Base Oil | Balance | Balance |

Industrial lubrication applications in which the compounds of formula (I), and lubricant additive concentrates comprising the same, can be used include hydraulic oils, industrial gear oils, windturbine oils, slideway machines oils, circulation oils and steam turbine oils, gas turbine oils, gear oils, compressor oils, mist oils and machine tool lubricants.

The compounds of formula (I), and lubricant additive concentrates comprising the same, can be used in transmission fluids. These fluids include automotive fluids such as manual transmission fluids, automatic transmission fluids, continuously variable transmission fluids, power steering fluids and power brake fluids. Compounds of formula (I) can also be incorporated into greases such as automotive, industrial and aviation greases, and automobile chassis lubricants.

The compounds of formula (I), and lubricant additive concentrates comprising the same, can be used in automotive gear or axle oils. Typical of such oils are automotive spiral-bevel and worm-gear axle oils which operate under extreme pressures, load and temperature conditions, hypoid gear oils operating under both high speed, low-torque and low-speed, high torque conditions.

Engine oils containing the compounds of formula (I) are also contemplated by the invention. Such oils include passenger car motor oils, heavy duty diesel engine oils, marine engine oils, locomotives, and high speed automotive diesel engines.

The invention also provides a method of lubricating metal surfaces. Lubricating metal surfaces with lubricant compositions of the present invention can reduce wear and/or friction between the metal surfaces when moving. In one embodiment, the metal surfaces being lubricated can be a machine part. The machine part can comprise an axle, a differential, an engine, a manual transmission, an automatic transmission, a continuously variable transmission, a clutch, a hydraulic apparatus, an industrial gear, a windturbine gear box, a slideway apparatus, and/or a turbine.

The invention further provides for a method of lubricating a driveline, industrial, or metalworking device comprising lubricating the driveline, industrial or metalworking device with a lubricant composition comprising a compound of formula (I).

EXAMPLES

Compounds of formula (I) can be prepared using the synthetic route described in Scheme 1. One or more dialkyl phosphites (II and II') are reacted with one or more carbonyl compound (III and III') and a primary amine (IV) which produces compound with formula (I) with the removal of water.

$R^1$ and $R^{10}$ are the same or different and are independently selected from $C_1$-$C_{20}$ linear alkyl, $C_2$-$C_{20}$ linear alkenyl, $C_3$-$C_{20}$ branched alkyl, and $C_3$-$C_{20}$ branched alkenyl; n is an integer from 1 to 7; each of $R^2$, $R^3$, $R^4$, $R^5$, $R^6$, $R^7$, $R^8$, and $R^9$ is the same or different and is each independently selected from H, $C_1$-$C_{10}$ linear alkyl, $C_2$-$C_{10}$ linear alkenyl, $C_3$-$C_{10}$ branched alkyl, and $C_3$-$C_{10}$ branched alkenyl; X is selected from the group consisting of H, hydroxy, and $N(R^{11})(R^{12})$, and $R^{11}$ and $R^{12}$ are the same or different and are each independently selected from the group consisting of H, hydroxy, alkyl, alkenyl, and alkynyl.

Compound 2

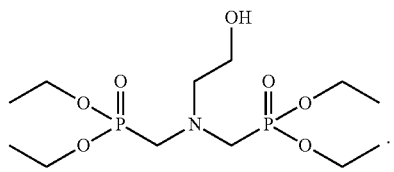

Scheme 1

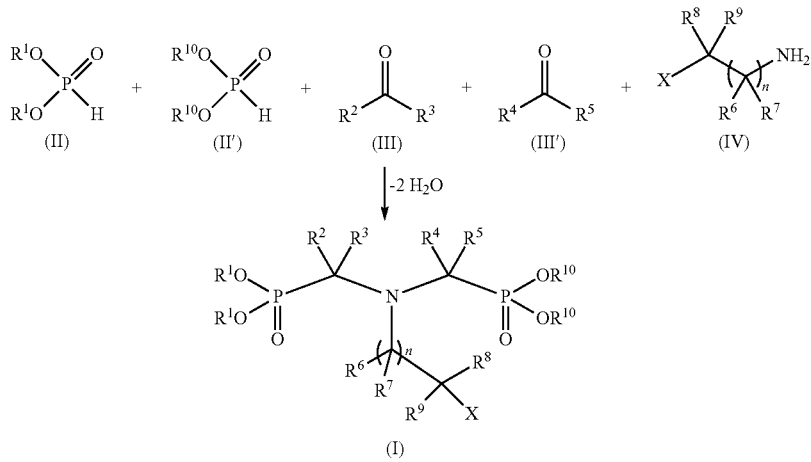

Compound 1

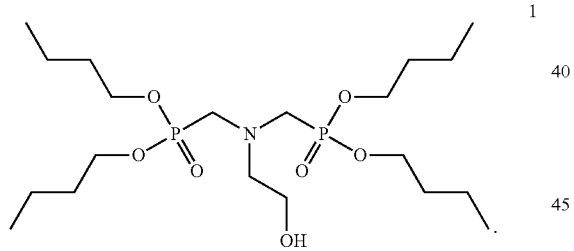

Compound 1 ($R^1$, $R^{10}$=n-butyl, $R^2$, $R^3$, $R^4$, $R^5$, $R^6$, $R^7$, $R^8$, and $R^9$=H, X=OH, n=1) was synthesized from di-n-butyl phosphite, formaldehyde (in the form of paraformaldehyde) and monoethanol amine. Under nitrogen, paraformaldehyde (118 g, 3.93 mol) was slowly added to a reactor containing monoethanol amine (120 g, 1.97 mol) at 60° C. After the addition of paraformaldehyde, the reaction mixture was heated to 95° C. under vacuum (45 mmHg) while distilling water off. The mixture was then cooled to 60° C. after no more distillate was observed. Di-n-butyl phosphite (762.86 g, 3.93 mol) was added and allowed to react for 10 hrs at 65° C. to give Compound 1. The structure of the compound was confirmed by P-31, H, and C-13 NMR spectroscopy as well as LC-MS (m/z=474.27 (M+1)). All NMR chemical shifts (δ) are given in ppm. $^1$H NMR δ 4.1 (8H), 3.6 (2H), 3.2 (4H), 3.0 (2H), 1.7 (8H), 1.4 (8H), 0.9 (12H). $^{13}$C NMR δ 65.78, 60.12, 59.12, 50.9, 32.71, 18.76, 13.61. 31P NMR δ 25.50.

Compound 2 ($R^1$, $R^{10}$=ethyl, $R^2$, $R^3$, $R^4$, $R^5$, $R^6$, $R^7$, $R^8$, and $R^9$=H, X=OH, n=1) can be prepared in a similar fashion to Compound 1 but using diethyl phosphite (361.75 g, 2.62 mol), paraformaldehyde (78.61 g, 2.62 mol), and monoethanol amine (80.13 g, 1.31 mol).

Compound 3

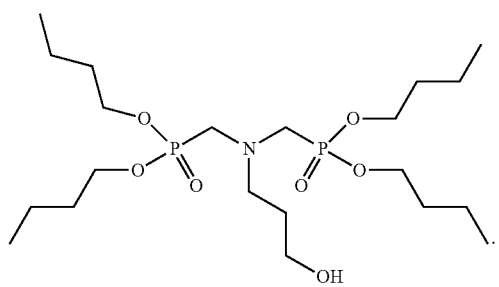

Compound 3 ($R^1$, $R^{10}$=butyl, $R^2$, $R^3$, $R^4$, $R^5$, $R^6$, $R^7$, $R^8$, and $R^9$=H, X=OH, n=2) can be prepare similar to Compound 1 but using di-n-butyl phosphite (582.28 g, 3.00 mol), paraformaldehyde (90.05 g, 3.00 mol), and 3-aminopropanol (112.67 g, 1.50 mol).

Compound 4

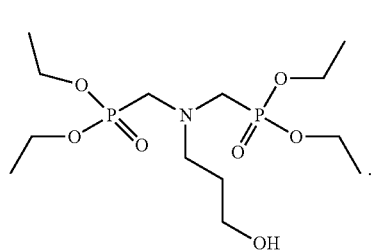

Compound 4 (R$^1$, R$^{10}$=ethyl, R$^2$, R$^3$, R$^4$, R$^5$, R$^6$, R$^7$, R$^8$, and R$^9$=H, X=OH, n=2) can be prepare similar to Compound 1 but using diethyl phosphite (350 g, 2.54 mol), paraformaldehyde (76.4 g, 2.54 mol), and 3-aminopropanol (95.1 g, 1.27 mol).

Compound 5

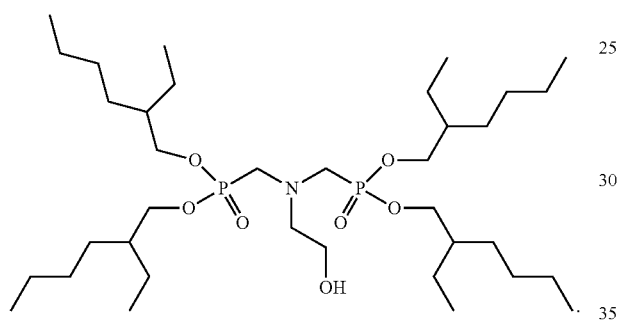

Compound 5 (R$^1$, R$^{10}$=2-ethylhexyl, R$^2$, R$^3$, R$^4$, R$^5$, R$^6$, R$^7$, R$^8$, and R$^9$=H, X=OH, n=1) can be prepared in a similar fashion to Compound 1 but using bis(2-ethylhexyl) phosphite (500 g, 1.63 mol), paraformaldehyde (49.1 g, 1.63 mol), and monoethanol amine (50 g, 0.82 mol).

Compound 6

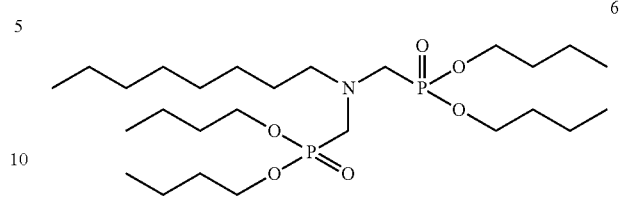

Compound 6 (R$^1$, R$^{10}$=butyl, R$^2$, R$^3$, R$^4$, R$^5$, R$^6$, R$^7$, R$^8$, and R$^9$, X=H, n=7) can be prepared in a similar fashion to Compound 1 but using di-n-butyl phosphite (388.2 g, 2.00 mol), paraformaldehyde (60.03 g, 2.00 mol), and n-octyl amine (129.25 g, 1.00 mol).

Compound 7

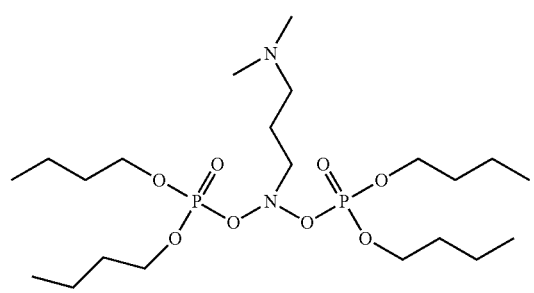

Compound 7 (R$^1$, R$^{10}$=butyl, R$^2$, R$^3$, R$^4$, R$^5$, R$^6$, R$^7$, R$^8$, and R$^9$=H, X=N(CH$_3$)$_2$, n=2) can be prepared in a similar fashion to Compound 1 but using di-n-butyl phosphite (543.52 g, 2.80 mol), paraformaldehyde (84.04 g, 2.80 mol), and 3-(dimethylamino)-propyl amine (143.05 g, 1.40 mol).

Compound 8

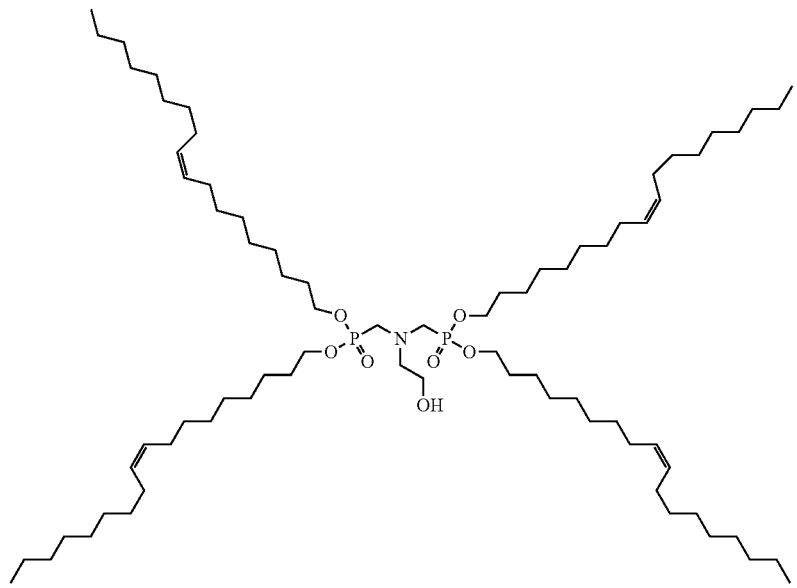 [SMILES: CCCCCCCC/C=C\CCCCCCCCOP(=O)(CN(CCO)CP(=O)(OCCCCCCCC/C=C\CCCCCCCC)OCCCCCCCC/C=C\CCCCCCCC)OCCCCCCCC/C=C\CCCCCCCC]

Compound 8 ($R^1$, $R^{10}$=oleyl, $R^2$, $R^3$, $R^4$, $R^5$, $R^6$, $R^7$, $R^8$, and $R^9$=H, X=OH, n=1) can be prepared in a similar fashion to Compound 1 but using di-n-oleyl phosphite (800 g, 1.37 mol), paraformaldehyde (41.2, 1.37 mol), and monoethanol amine (41.9, 0.69 mol).

Functional Studies

High Frequency Reciprocating Rig (HFRR)

Lubricant test fluids, each comprising one of Compounds 1-8 above, were subjected to HFRR testing (according to ASTM-D6079-11), modified to test the compounds at 80° C. using a 400 g mass with a 1-mm stroke at a frequency of 20 Hz for three minutes. Wear scar, produced on an oscillating ball from contact with a stationary disk immersed in the fluid operating under defined and controlled conditions, was evaluated and measured in microns. The HFFR testing apparatus consists of a vibrator, heating bath, specimen holder, test ball and test disk. To form the lubricant test fluids, each of the Compounds 1 through 8 were added to Group I mineral oil. The lubricant test fluids each had a viscosity of ISO 100 VG and contained 300 ppm of phosphorus delivered by the respective Compounds 1-8 prepared as described above.

A 2-mL test specimen of lubricant (containing Group I mineral oil and one of Compounds 1-8) is placed in the test reservoir of the HFRR. A vibrator arm holding the non-rotating steel ball and loaded with a 400-g mass is lowered until it contacts the test disk completely submerged in the lubricant fluid. When the fluid temperature has stabilized, the ball is caused to rub against the disk with a 1-mm stroke at a frequency of 20 Hz for three minutes. Test fluid temperature is maintained and ambient relative humidity is maintained between 30% and 85%. An image of the wear scar is captured using a microscope digital camera, and the dimensions of the major and minor axes of the wear scar are measured and recorded, and the mean wear scar diameter (MWSD) is calculated.

TABLE 1

HFRR Testing

| Example | | HFRR MWSD (μm) | HFRR Coefficient of Friction (μ) |
|---|---|---|---|
| Comparative Example | Group I mineral oil only | 161 | 0.15 |
| 1 | Compound 1 | 110 | 0.12 |
| 2 | Compound 2 | 0* | 0.11 |
| 3 | Compound 3 | 151 | 0.12 |
| 4 | Compound 4 | 142 | 0.12 |
| 5 | Compound 5 | 92 | 0.14 |
| 6 | Compound 6 | 138 | 0.13 |
| 7 | Compound 7 | 115 | 0.14 |
| 8 | Compound 8 | 153 | 0.13 |

*No detectable wear

In Table 1 above, HFRR test results for Compounds 1-8 show that all lubricant compositions containing the compounds of formula (I) demonstrate both reduced wear and reduced friction as compared to the same lubricant composition without the compounds of formula (I).

MTM-SLIM

The Mini Traction Machine-Space Layer Imaging Machine (MTM-SLIM) measures the frictional properties of lubricated contact surfaces. In the MTM-SLIM configuration, a 19.05 mm steel ball is loaded against the face of a steel disc measuring 46 mm in diameter. The ball and disc are attached to a shaft and submerged in lubricant. The ball and disc are driven independently to create rolling and sliding contact. Optical interferometry is used to measure the formation of additive film growth on a contact surface during the test. Sensors measure the applied load, lubricant temperature, and wear on the contact surfaces. Frictional force between the ball and disc is measured by a force transducer.

A typical fully formulated industrial gear fluid containing Compound 1 was tested in MTM-SLIM in a typical ISO VG 100 gear oil fluid. The fluid components and the respective treat rates are shown in Table 2 below. The test conditions included a 50% slide to roll ratio (sliding velocity to rolling velocity) such that the ball is rotating at a faster speed than the disc. The ball speed was 125 mm/s and the disc speed was 75 mm/s. The tests were run at a temperature of 100° C. for one (1) hour and the coefficient of friction was measured. The conditions were held constant for the duration of the test. An interference image is captured periodically during the test to calculate the thickness of the tribofilm layer with respect to time. As shown in Table 3, in the first test, 2 GPa contact pressure was applied with a load of 20N. In the second test, 3 GPa contact pressure was applied with a load of 75N.

TABLE 2

ISO 100 VG Industrial Gear Fluid

| Component | Weight % |
|---|---|
| Compound 1 | 0.24% |
| Group 1 Mineral Oil | 98.307% |
| Sulfurized Olefin Extreme Pressure Agent | 0.71% |
| Succinimide Dispersant | 0.25% |
| Heterocyclic Corrosion Inhibitor | 0.06% |
| Fatty Acid Corrosion Inhibitor | 0.03% |
| Phenolic Anti-oxidant | 0.15% |
| EO/PO Copolymer Demulsifier | 0.003% |
| Acrylate Pour Point Depressant | 0.25% |

The results of the MTM-SLIM testing are shown in Table 3. The results shown in this table can be extrapolated to the other compounds of formula (I). The results indicate that a phosphorus containing molecules of the compounds of formula (I) form phosphorus film under high loads. Likewise, a fluid containing a compound of formula (I) forms a phosphorus film under high loads.

TABLE 3

ISO 100 VG Industrial Gear Fluid

| Contact Pressure (GPa) | Film Thickness (nm) | % Phos in Film |
|---|---|---|
| 2 | 9 | 0.27 |
| 3 | 28 | 1.39 |

FVA Micropitting

Micropitting is a fatigue failure of the surface material that is used in gear systems. Additives in gear fluids are required to prevent micropitting from occurring. The micropitting test GF-C/8.3/90 according to FVA-Information sheet 54/7 is used to measure the micropitting load capacity of a lubricant and consist of two parts; a load stage test followed by an endurance test.

A typical fully formulated industrial gear fluid containing Compound 1 and having an ISO VG 100 was tested in the micropitting test GF-C/8.3/90 according to FVA-Information sheet 54/7. The fluid components and the respective treat rates are shown in Table 4 below. The test was modified such that only the load stage portion of the test was conducted. This is sufficient in determining the micropitting load capacity of a fluid.

TABLE 4

ISO 100 VG Industrial Gear Fluid

| Component | Weight % |
|---|---|
| Compound 1 | 0.24% |
| Group 1 Mineral Oil | 98.017% |
| Sulfurized Olefin Extreme Pressure Agent | 1.00% |
| Succinimide Dispersant | 0.25% |
| Heterocyclic Corrosion Inhibitor | 0.06% |
| Fatty Acid Corrosion Inhibitor | 0.03% |
| Phenolic Anti-oxidant | 0.15% |
| EO/PO Copolymer Demulsifier | 0.003% |
| Acrylate Pour Point Depressant | 0.25% |

Figure 2:
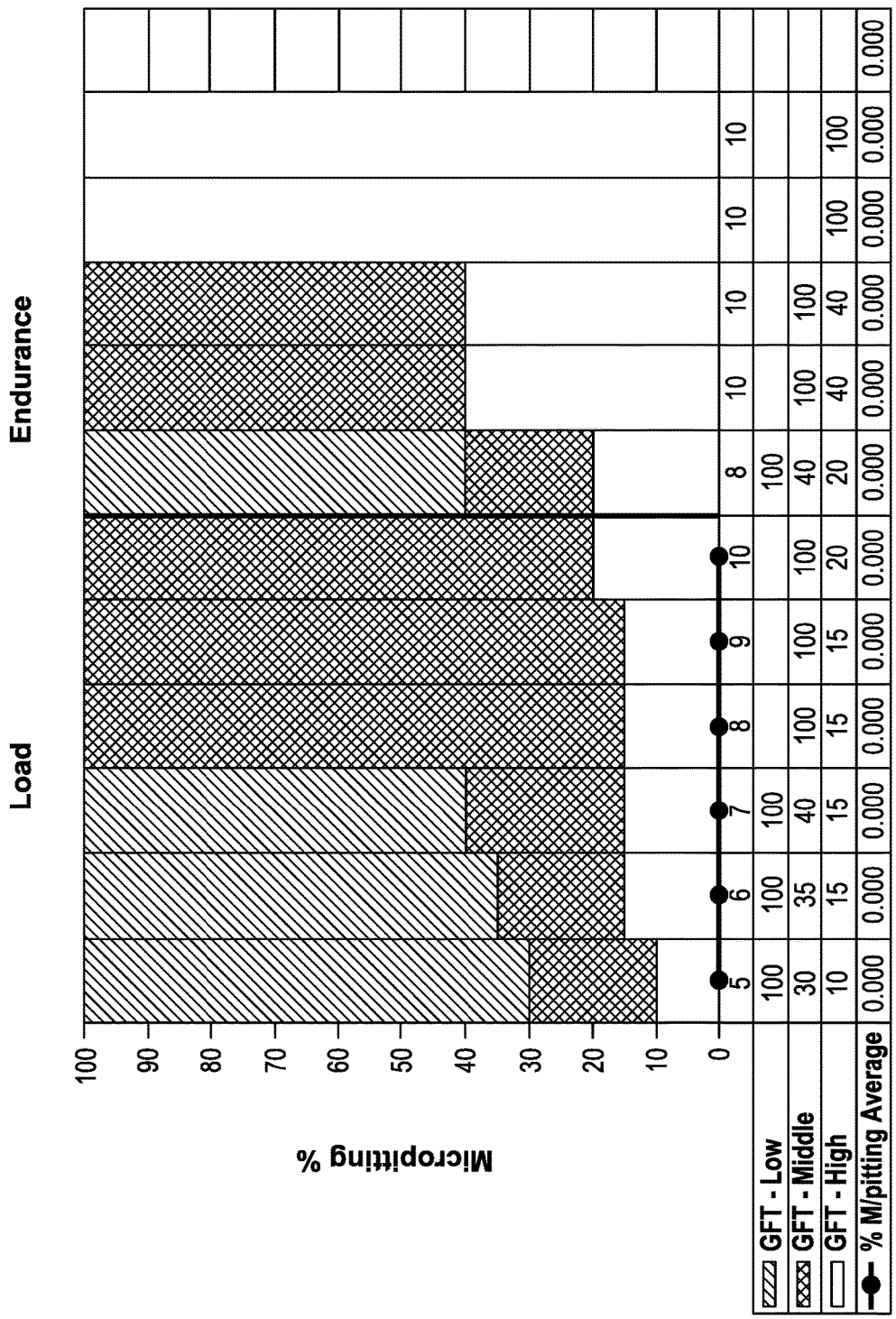
FIG. 2 represents percent micropitting area (GF) in a micropitting test for an embodiment of the invention.
Figure 3:
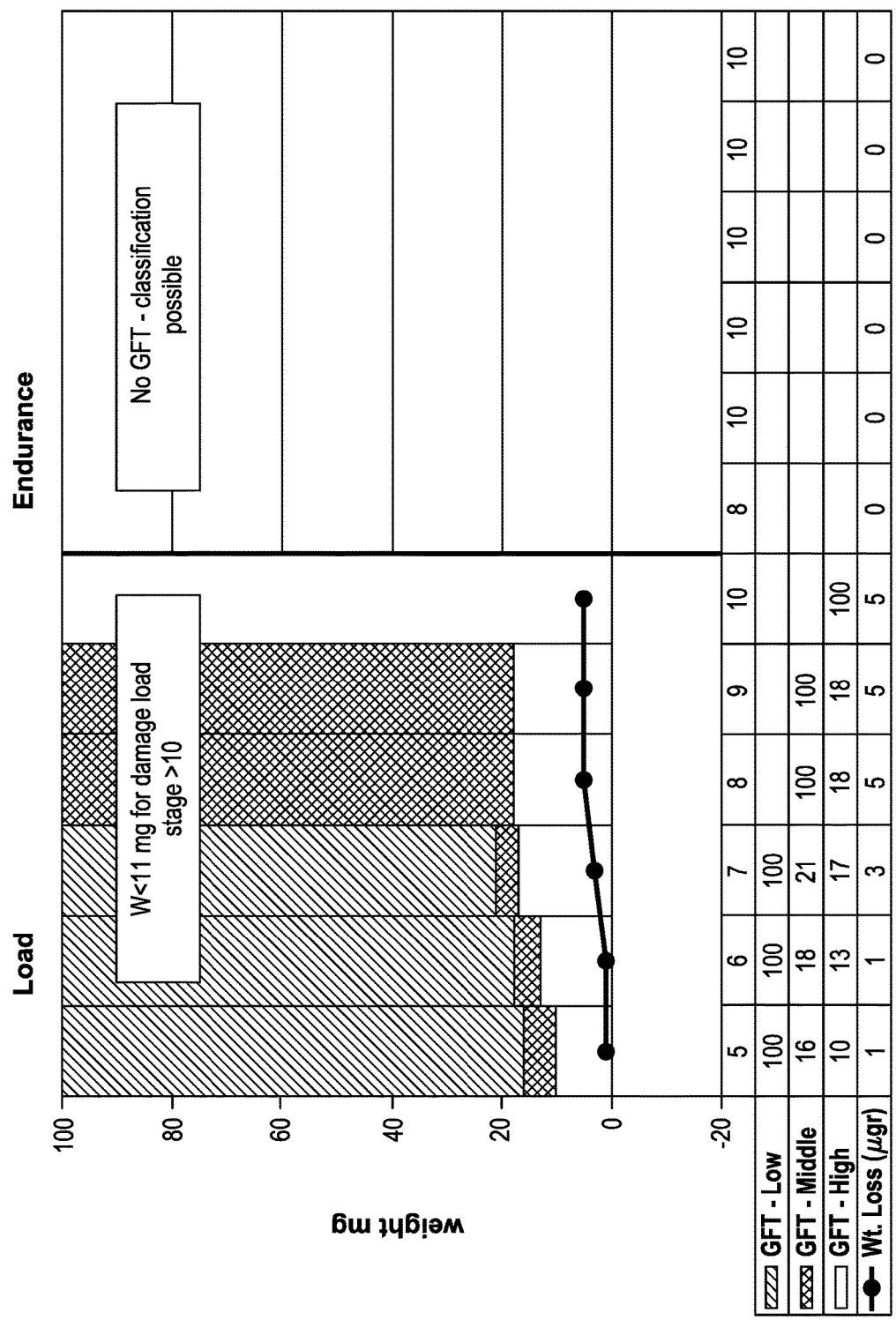
FIG. 3 represents weight loss (W) in a micropitting test for an embodiment of the invention.

The results of the micropitting test are shown in FIGS. 1, 2 and 3. FIG. 1 shows an average profile deviation (ffm) caused by micropitting. As indicated, the load stage of the test running time (16 h/load stage) is shown on the left whereas the endurance test running time (80 h/load stage) is shown on the right. The testing conditions were as follows:
 a. Gear type: C
 b. Pitch line velocity: 8.3 m/s
 c. Lubricant injection temperature: 90° C.

FIG. 2 shows the percent (%) micropitting area GF. As indicated, the load stage of the test running time (16 h/load stage) is shown on the left whereas the endurance test running time (80 h/load stage) is shown on the right. The test conditions were the same as those indicated for FIG. 1 above.

FIG. 3 shows weight loss (W). As indicated, the load stage of the test running time (16 h/load stage) is shown on the left whereas the endurance test running time (80 h/load stage) is shown on the right. The test conditions were the same as those indicated for FIG. 1 above.

As shown in FIGS. 1-3, gears lubricated with the test fluid had a low average profile deviation, no detectable micropitting, and low weight loss during the load stage. These results indicate that compounds of formula (I), including Compound 1, provide good to excellent micropitting protection as compared to the same lubricant compositions without compounds of formula (I). Fluids containing compounds of formula (I), including Compound 1, can be classified as "high micropitting load capacity" fluids.

FAG FE8 Bearing Test

Many gear systems contain roller bearings elements. Proper lubrication of these bearings are required to prevent wear under high loads. The ability of a lubricant to protect the bearing element can be tested by the FAG FE8 bearing test (DIN 51819-3; 2 runs; each run 80 kN for 80 hrs at 80° C.).

A typically fully formulated industrial gear fluid containing Compound 1 and having an ISO VG 100 was tested in the above referenced FAG FE8 Bearing Test. The fluid components and the respective treat rates are shown in Table 4 above. At the conclusion of the test, an average of only 1 mg of roller bearing wear was observed. A pass rating for this test is 30 mg or less.

Multiple Temperature High Frequency Reciprocating Rig (HFRR)

Fully formulated hydraulic lubricating fluids comprising Compound 1 above, dioleyl hydrogen phosphite (DOHP), or dimethyl octadecylphosphonate (DMOP) were subjected to multiple temperature HFRR testing (according to ASTM-D6079-11), modified to test the compounds at 70° C., 100° C. and 130° C. using 4N friction force, a 400 g mass with a 1-mm stroke at a frequency of 20 Hz for three minutes at each temperature. Wear scar, produced on an oscillating ball from contact with a stationary disk immersed in the fluid operating under defined and controlled conditions, was evaluated and measured in microns. The HFFR testing apparatus consists of a vibrator, heating bath, specimen holder, test ball and test disk. The components of the test fluids are listed in Table 5 as wt. % of the finished fluid.

TABLE 5

Multi Temp HFRR Testing

| Component | Fluid A | Fluid B | Fluid C | Fluid D | Fluid E | Fluid F |
|---|---|---|---|---|---|---|
| corrosion inhibitor system | .0900 | .0900 | .0900 | .0900 | .0900 | .0900 |
| phenolic antioxidant | 0.2000 | 0.2000 | 0.2000 | 0.2000 | 0.2000 | 0.2000 |
| ashless PIB dispersant system | 0.462 | 0.462 | 0.462 | 0.462 | 0.462 | 0.462 |
| nonylated diphenylamine antioxidant | 0.0350 | 0.0350 | 0.0350 | 0.0350 | 0.0350 | 0.0350 |
| rust inhibitor | 0.0870 | 0.0870 | 0.0870 | 0.0870 | 0.0870 | 0.0870 |
| calcium phenate detergent | 0.1030 | 0.1030 | 0.1030 | 0.1030 | 0.1030 | 0.1030 |
| ashless antiwear system | 0.1400 | 0.1400 | 0.1400 | 0.1400 | 0.1400 | 0.1400 |
| defoamer, non-ionic surfactant | 0.0090 | 0.0090 | 0.0090 | 0.0090 | 0.0090 | 0.0090 |
| DOHP | 0.0600 | 0.1200 | | | | |
| DMOP | | | 0.0600 | 0.1200 | | |
| Compound 1 | | | | | 0.0600 | 0.1200 |
| Group III base oil | 98.814 | 98.754 | 98.814 | 98.754 | 98.814 | 98.754 |

A 2-mL test specimen of lubricant A-F is placed in the test reservoir of the HFRR. A vibrator arm holding the non-rotating steel ball and loaded with a 400-g mass is lowered until it contacts the test disk completely submerged in the lubricant fluid. When the fluid temperature has stabilized, the ball is caused to rub against the disk with a 1-mm stroke at a frequency of 20 Hz for three minutes at each test temperature, where the rubbing is paused during each temperature change. Ambient relative humidity is maintained between 30% and 85%. An image of the wear scar is captured using a microscope digital camera, the dimensions of the major and minor axes of the wear scar are measured and recorded, and the mean wear scar diameter (MWSD) is calculated. Results for Fluids A-F and control are in Table 6.

TABLE 6

Multi Temp HFRR Results

| | Control* | Fluid A | Fluid B | Fluid C | Fluid D | Fluid E | Fluid F |
|---|---|---|---|---|---|---|---|
| MWSD/μm | 221.0 | 193.5 | 177.0 | 188.0 | 186.0 | 166.0 | 123.0 |

*Control fluid is identical to Fluids A-F but without DOHP, DMOP or compound 1.

The compounds of the present invention provide a lower MWSD than conventional components in the multi-temperature HFRR test.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

What is claimed:

1. A compound of formula (I)

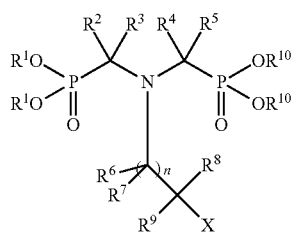

wherein each of $R^1$ and $R^{10}$ is the same or different and independently selected from $C_1$-$C_{20}$ linear alkyl, $C_2$-$C_{20}$ linear alkenyl, $C_3$-$C_{20}$ branched alkyl, and $C_3$-$C_{20}$ branched alkenyl;

n is an integer from 1 to 7;

each of $R^2$, $R^3$, $R^4$, $R^5$, $R^6$, $R^7$, $R^8$, and $R^9$ is the same or different and is each independently selected from H, $C_1$-$C_{10}$ linear alkyl, $C_2$-$C_{10}$ linear alkenyl, $C_3$-$C_{10}$ branched alkyl, and $C_3$-$C_{10}$ branched alkenyl;

X is selected from the group consisting of H, hydroxy, and $N(R^{11})(R^{12})$; and $R^{11}$ and $R^{12}$ are the same or different and are each independently selected from the group consisting of H, hydroxy, alkyl, alkenyl, and alkynyl, wherein $R^1$ and $R^{10}$ are not both ethyl.

2. The compound of claim 1, wherein each of $R^1$ and $R^{10}$ is the same.

3. The compound of claim 2, wherein each of $R^1$ and $R^{10}$ is n-butyl.

4. The compound of claim 2, wherein each of $R^1$ and $R^{10}$ is 2-ethyl hexyl.

5. The compound of claim 2, wherein each of $R^1$ and $R^{10}$ is oleyl.

6. The compound of claim 1, wherein each of $R^2$, $R^3$, $R^4$, and $R^5$ are H.

7. The compound of claim 1, wherein each of $R^6$, $R^7$, $R^8$, and $R^9$ are H.

8. The compound of claim 1, wherein n is 1 or 2.

9. The compound of claim 1, wherein each of $R^1$ and $R^{10}$ is $C_1$-$C_{10}$ linear alkyl.

10. The compound of claim 1, wherein X is hydroxyl.

11. The compound of claim 1, wherein X is $N(R^{11})(R^{12})$, and $R^{11}$ and $R^{12}$ are the same or different and are $C_1$-$C_4$ alkyl.

12. The compound of claim 1, wherein $R^{11}$ and $R^{12}$ are both methyl.

13. The compound of claim 1, wherein X is H.

14. The compound of claim 1, wherein (a) each of $R^1$ and $R^{10}$ is the same and is selected from $C_1$ and $C_3$-$C_{20}$ linear alkyl;

(b) each of $R^2$, $R^3$, $R^4$, $R^5$, $R^6$, $R^7$, $R^8$, and $R^9$ are H; and (c) n is 1 or 2.

15. The compound of claim 1, wherein the compound of formula (I) is selected from:

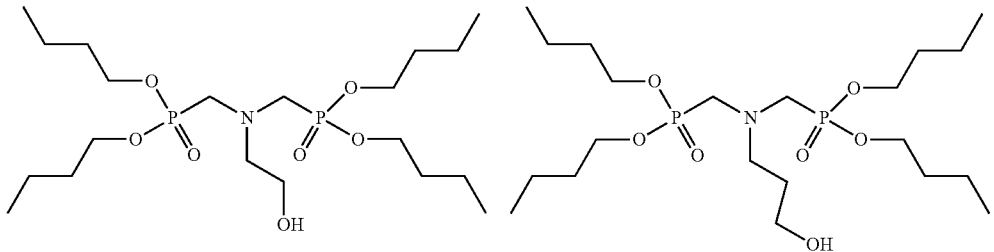

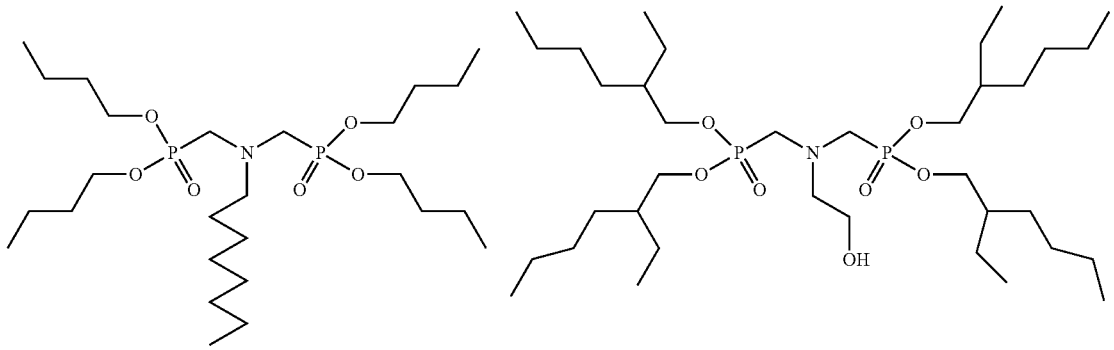

-continued

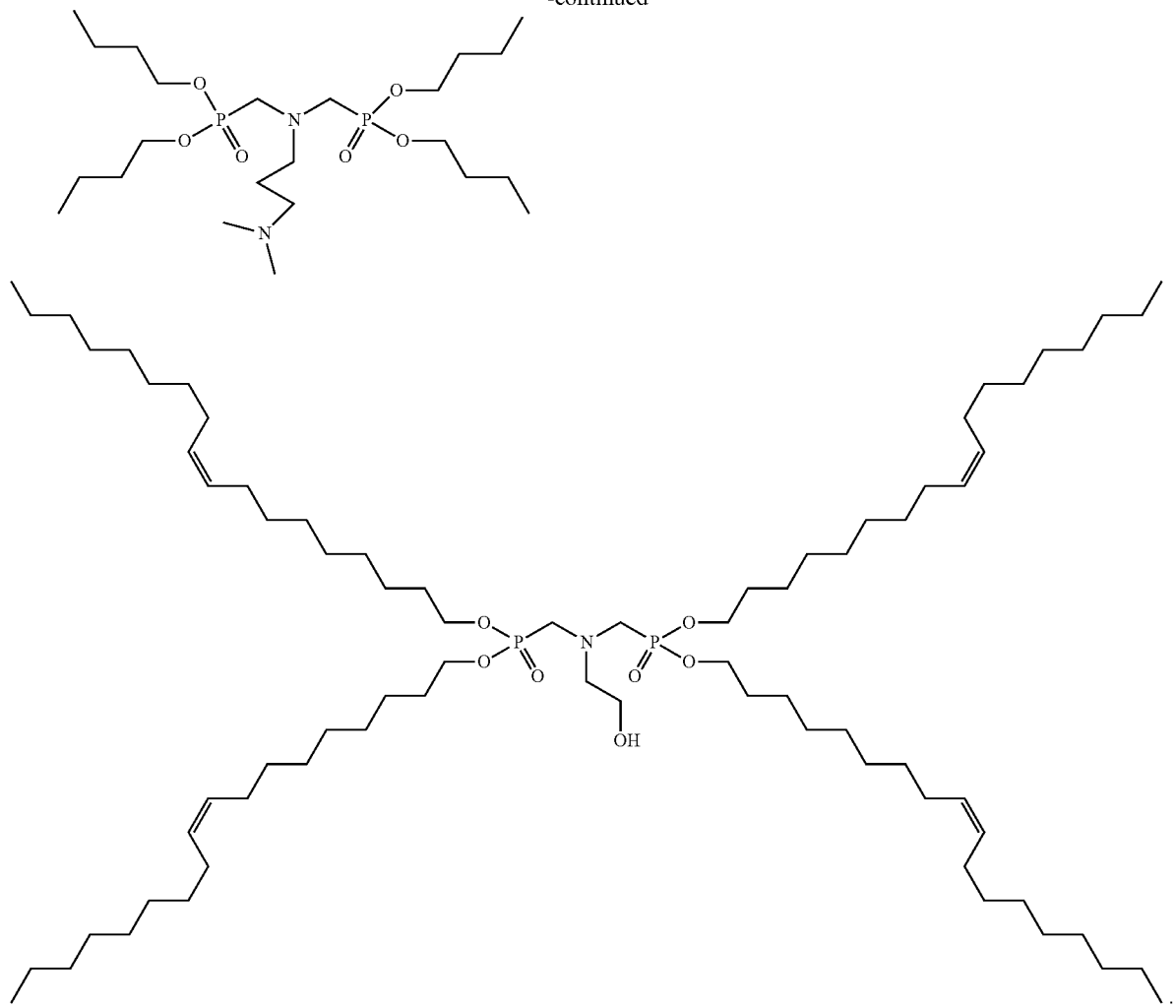

16. The compound of claim 1, wherein the compound of formula (I) is selected from:

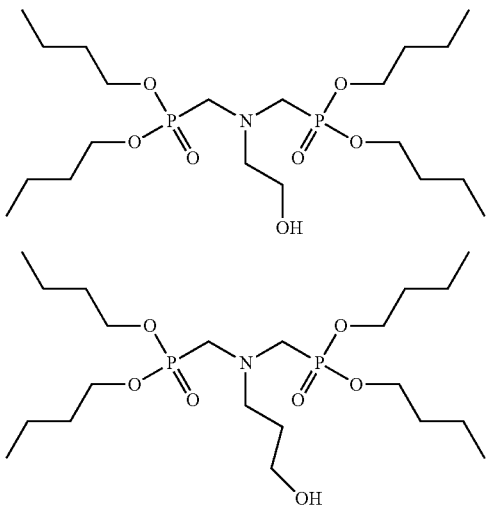

17. A lubricant additive concentrate comprising a compound according to claim 1.

18. The lubricant additive concentrate of claim 17, wherein the lubricant additive concentrate further comprises one or more additive components selected from the group consisting of an antioxidant, an additional antiwear agent, a corrosion inhibitor, a detergent, an extreme pressure agent, a dispersant, a viscosity index improver, and a friction modifier.

19. A lubricant additive concentrate comprising a compound according to claim 16.

20. The lubricant additive concentrate of claim 19, wherein the lubricant additive concentrate further comprises one or more additive components selected from the group consisting of an antioxidant, an additional antiwear agent, a corrosion inhibitor, a detergent, an extreme pressure agent, a dispersant, a viscosity index improver, and a friction modifier.

21. A lubricant composition comprising:
a) a major amount of base oil; and
b) a compound according to claim 1.

22. A lubricant composition comprising:
a) a major amount of base oil; and
b) the lubricant additive concentrate of claim 17.

23. The lubricant composition of claim 21, wherein the compound is present in an amount from about 0.010 wt % to about 5 wt % based on the total weight of the lubricant composition.

24. The lubricant composition of claim 21, wherein the lubricant composition is fully formulated hydraulic lubricating fluid.

25. A method of lubricating moving metal surfaces of a machine part, comprising lubricating the surfaces with a lubricant composition of claim 21.

26. A method of reducing wear between moving metal surfaces of a machine part comprising lubricating the machine part with a lubricant composition of claim 21.

27. A method of reducing friction between moving metal surfaces of a machine part comprising lubricating the machine part with a lubricant composition of claim 21.

28. The method of claim 25, wherein the machine part is selected from one or more of an industrial gear, a windturbine gear, an axle, a differential, an engine, a crankshaft, a transmission, a clutch, a hydraulic apparatus, a slideway apparatus, and a turbine.

29. The method of claim 28, wherein the machine part is a hydraulic apparatus.

\* \* \* \* \*